(12) United States Patent
Douk et al.

(10) Patent No.: US 7,044,958 B2
(45) Date of Patent: May 16, 2006

(54) TEMPORARY DEVICE FOR CAPTURING EMBOLIC MATERIAL

(75) Inventors: Nareak Douk, Lowell, MA (US);
Nasser Rafiee, Andover, MA (US);
Peter G. Strickler, Tewksbury, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 228 days.

(21) Appl. No.: 09/922,996

(22) Filed: Aug. 1, 2001

(65) Prior Publication Data

US 2002/0143361 A1     Oct. 3, 2002

Related U.S. Application Data

(63) Continuation-in-part of application No. 09/824,832, filed on Apr. 3, 2001.

(51) Int. Cl.
*A61M 29/00*     (2006.01)

(52) U.S. Cl. ...................................... 606/200

(58) Field of Classification Search ............... 606/113, 606/114, 151, 191, 200, 194, 127, 154
See application file for complete search history.

(56) References Cited

U.S. PATENT DOCUMENTS

| | | | |
|---|---|---|---|
| 3,996,938 A | 12/1976 | Clark, III | |
| 4,921,484 A | 5/1990 | Hillstead | |
| 4,926,858 A | 5/1990 | Gifford, III et al. | |
| 5,160,342 A | 11/1992 | Reger et al. | |
| 5,265,622 A | 11/1993 | Barbere | |
| 5,329,942 A | 7/1994 | Gunther et al. | |
| 5,376,094 A | 12/1994 | Kline | |
| 5,483,022 A | 1/1996 | Mar | |
| 5,569,184 A | 10/1996 | Chum et al. | |
| 5,628,787 A | 5/1997 | Mayer | |
| 5,630,840 A | 5/1997 | Mayer | |
| 5,658,309 A | * 8/1997 | Berthiaume et al. | ........ 606/192 |

(Continued)

FOREIGN PATENT DOCUMENTS

EP     0 771 549 A1     5/1997

(Continued)

OTHER PUBLICATIONS

Hodgson, D.E. et al; "Augmented Properties of NiTi Wire by 'Filling' with Selected Metals" *SMST-97: Proceedings of the Second International Conference on Shape Memory and Superelastic Technologies*, (1997) no month, pp. 461-465.

*Primary Examiner*—Julian W. Woo
*Assistant Examiner*—Victor Nguyen
(74) *Attorney, Agent, or Firm*—James F. Crittenden (57) ABSTRACT

The present invention is a temporary device for capturing and removing embolic material during interventional procedures, such as angioplasty or stent deployment. A self-closing, tubular capture element, which may be either a filter or an occluder, is mounted near the distal end of a guidewire. The guidewire is capable of guiding a therapeutic catheter. Relative displacement of the capture element ends causes transformation of the capture element between a closed configuration and a deployed configuration that spans the vessel to be treated. A latch fixed to the guidewire temporarily retains the capture element in the deployed configuration. A first hollow rod slides over the guidewire to deploy the capture element and engage the capture element proximal end with the latch. A second hollow rod slides over the guidewire to release the latch and close the capture element.

26 Claims, 9 Drawing Sheets

U.S. PATENT DOCUMENTS

| | | |
|---|---|---|
| 5,679,470 A | 10/1997 | Mayer |
| 5,725,570 A | 3/1998 | Heath |
| 5,765,418 A | 6/1998 | Rosenberg |
| 5,800,511 A | 9/1998 | Mayer |
| 5,814,064 A | 9/1998 | Daniel et al. |
| 5,824,056 A | 10/1998 | Rosenberg |
| 5,824,077 A | 10/1998 | Mayer |
| 5,827,324 A * | 10/1998 | Cassell et al. ............... 606/200 |
| 5,910,154 A | 6/1999 | Tsugita et al. |
| 5,911,734 A | 6/1999 | Tsugita et al. |
| 5,925,060 A | 7/1999 | Forber |
| 5,935,139 A | 8/1999 | Bates |
| 5,972,019 A * | 10/1999 | Engelson et al. ............ 606/200 |
| 6,001,118 A * | 12/1999 | Daniel et al. ................ 606/200 |
| 6,027,520 A | 2/2000 | Tsugita et al. |
| 6,042,598 A | 3/2000 | Tsugita et al. |
| 6,053,932 A | 4/2000 | Daniel et al. |
| 6,056,769 A | 5/2000 | Epstein et al. |
| 6,059,814 A | 5/2000 | Ladd |
| 6,066,158 A | 5/2000 | Engelson et al. |
| 6,096,053 A | 8/2000 | Bates |
| 6,099,549 A | 8/2000 | Bosma et al. |
| 6,152,946 A | 11/2000 | Broome et al. |
| 6,165,200 A | 12/2000 | Tsugita et al. |
| 6,171,327 B1 | 1/2001 | Daniel et al. |
| 6,179,859 B1 | 1/2001 | Bates et al. |
| 6,221,086 B1 | 4/2001 | Forber |
| 6,238,415 B1 | 5/2001 | Sepetka et al. |
| 6,245,012 B1 | 6/2001 | Kleshinski |
| 6,258,115 B1 | 7/2001 | Dubrul |
| 6,277,138 B1 | 8/2001 | Levinson et al. |
| 6,346,116 B1 * | 2/2002 | Brooks et al. ............... 606/200 |
| 6,371,971 B1 | 4/2002 | Tsugita et al. |
| 6,537,296 B1 | 3/2003 | Levinson et al. |
| 2002/0103501 A1 | 8/2002 | Diaz et al. |

FOREIGN PATENT DOCUMENTS

| | | |
|---|---|---|
| WO | WO 96/01591 A1 | 1/1996 |
| WO | WO 99/22673 A1 | 5/1999 |
| WO | WO 99/23976 A1 | 5/1999 |
| WO | WO 99/44510 A1 | 6/1999 |
| WO | WO 00/67664 A1 | 11/2000 |
| WO | WO 00/67667 A1 | 11/2000 |
| WO | WO 00/67671 A1 | 11/2000 |
| WO | WO 01/08595 A1 | 2/2001 |
| WO | WO 01/45590 A2 | 6/2001 |
| WO | WO 01/45592 A1 | 6/2001 |
| WO | WO 01/49215 A2 | 7/2001 |

* cited by examiner

FIG. 20 ced emboli
TEMPORARY DEVICE FOR CAPTURING EMBOLIC MATERIAL

CROSS-REFERENCE TO RELATED APPLICATION

This patent application is a continuation-in-part of U.S. patent application Ser. No. 09/824,832 to Douk et al. filed Apr. 3, 2001 entitled "Temporary Intraluminal Filter Guidewire and Methods of Use."

FIELD OF THE INVENTION

The present invention relates generally to intraluminal devices for capturing particulate in the vessels of a patient. More particularly, the invention relates to a filter for capturing emboli in a blood vessel during an interventional vascular procedure and then removing the captured emboli from the patient after completion of the procedure. Furthermore, the invention concerns a capture element mounted on a guidewire that can also be used to direct an interventional catheter to a treatment site within a patient.

BACKGROUND OF THE INVENTION

A variety of treatments exists for dilating or removing atherosclerotic plaque in blood vessels. The use of an angioplasty balloon catheter is common in the art as a minimally invasive treatment to enlarge a stenotic or diseased blood vessel. When applied to the vessels of the heart, this treatment is known as percutaneous transluminal coronary angioplasty, or PTCA. To provide radial support to the treated vessel in order to prolong the positive effects of PTCA, a stent may be implanted in conjunction with the procedure.

Thrombectomy is a minimally invasive technique for removal of an entire thrombosis or a sufficient portion of the thrombosis to enlarge the stenotic or diseased blood vessel and may be accomplished instead of a PTCA procedure. Atherectomy is another well known minimally invasive procedure that mechanically cuts or abrades a stenosis within the diseased portion of the vessel. Alternatively, ablation therapies use laser or RF signals to superheat or vaporize the thrombus within the vessel. Emboli loosened during such procedures may be removed from the patient through the catheter.

During each of these procedures, there is a risk that emboli dislodged by the procedure will migrate through the circulatory system and cause infarction or strokes. Thus, practitioners have approached prevention of escaped emboli through use of occlusion devices, filters, lysing and aspiration techniques. For example, it is known to remove the embolic material by suction through an aspiration lumen in the treatment catheter or by capturing emboli in a filter or occlusion device positioned distal of the treatment area.

Prior art temporary filters or occlusion devices are associated with either a catheter or guidewire and are positioned downstream of the area to be treated. One prior art filter arrangement includes a dilatation balloon and a filter mounted on the same catheter. The filter is located distal to the dilatation balloon and consists of a filter material secured to resilient ribs. A filter balloon is located between the catheter exterior and the ribs. Inflation of the filter balloon extends the ribs outward across the vessel to form a trap for fragments loosened by the dilatation balloon. When the filter balloon is deflated, the resilient ribs retract against the catheter to retain the fragments during withdrawal of the catheter.

Another prior art device provides an expandable occlusion member mounted on a slender, elongate wire. The occlusion member is passed distal to the intended treatment site and expanded to obstruct the flow of bodily fluids during the procedure. An interventional catheter is guided to the treatment site over the wire and the vessel narrowing is enlarged. Any emboli produced are trapped upstream of the occlusion balloon. Bodily fluid containing the particulate is aspirated from the vessel, either through a dedicated lumen in the treatment catheter, or via a separate aspiration catheter that has been exchanged for the treatment catheter. Last, the occlusion member is collapsed and removed from the patient. The occlusion member may be an inflatable balloon or a mechanically expandable structure covered by a non-porous membrane.

Another prior art device includes a filter mounted on the distal portion of a hollow guidewire or tube. A moveable core wire is used to open and close the filter. The filter is secured at the proximal end to the tube and at the distal end to the core wire. Pulling on the core wire while pushing on the tube draws the ends of the filter toward each other, causing the filter framework between the ends to expand outward into contact with the vessel wall. Filter mesh material is mounted to the filter framework. To collapse the filter, the procedure is reversed; pulling on the tube while pushing on the core wire to draw the filter ends apart.

Another prior art device has a filter made from a shape memory material. The device is deployed by moving the proximal end of the filter towards the distal end. The filter is collapsed and withdrawn by sliding a sheath over the filter and then removing the sheath and filter together.

Another prior art filter device discloses a compressible polymeric foam filter mounted on a shaft that is inserted over a guidewire. The filter is inserted collapsed within a housing which is removed to deploy the filter once in position. The filter is retracted by inserting a large bore catheter over the shaft and the filter, and then removing the shaft, filter and catheter together.

Another prior art filter arrangement has a filter comprised of a distal filter material secured to a proximal framework. This filter is deployed in an umbrella manner with a proximal member sliding along the shaft distally to open the filter and proximally to retract the filter. A large separate filter sheath can be slid onto the shaft and the filter can be withdrawn into the sheath for removal from the patient.

Other known prior art filters are secured to the distal end of a guidewire with a tubular shaft. Stoppers are placed on the guidewire proximal and distal of the filter, allowing the filter to move axially independently of the guidewire. Sheaths are used to deploy and compress the filter.

A problem associated with prior art filter guidewires is the requirement for a sheath to envelop and collapse the filter before and after the treatment is performed. Sheaths that encase the filter often require large bores, with attendant bulky handling. It is time-consuming and cumbersome to exchange the sheath for the treatment catheter and to reverse this exchange step at the end of the procedure.

Another problem associated with guidewire-based devices in the prior art is that the clinician must decide whether or not to start the procedure with a filter (or occluder) guidewire. If the diseased conduit is particularly tortuous, the additional capture mechanism at the distal end of the guidewire may inhibit or interfere with initial crossing of the treatment site. In this case, the procedure may require initial negotiation with a standard guidewire, then advancement there over by the treatment catheter, then exchanging of the standard guidewire for a wire-based distal capture device. Besides the additional time and steps required, there is the extra cost of the two kinds of guidewires involved.

Finally, inflating occluding balloons on small diameter guidewires, such as those used in PTCA, requires the complexities of an external inflation accessory and a miniature sealing mechanism to sustain the balloon in occlusion mode while an interventional catheter is loaded over the proximal end of the guidewire.

With the above in mind, it is an object of the present invention to provide a temporary device for capturing embolic material that does not require an enveloping sheath to collapse the capture element for insertion or withdrawal.

Another object of the present invention is to provide a temporary device for capturing embolic material, wherein the device may be deployed and/or closed with a mechanism that is simple compared to the hydro-pneumatic devices of the prior art.

Another object of the present invention is to provide a temporary device for capturing embolic material, wherein an adapted guidewire may be used as a standard guidewire, then, as desired, a capture element may be introduced over the guidewire and deployed into apposition with the vessel of the patient.

BRIEF SUMMARY OF THE INVENTION

The present invention is a temporary device for capturing embolic material during intraluminal procedures. The device includes a capture element mounted adjacent the distal end of a guidewire used in the procedure. The capture element is a tubular assembly that expands in the middle region when the ends are forced toward each other. The capture element includes an expandable support structure which may be covered with an elastic membrane, optionally providing either an occluder device or a filter device. The support structure may comprise a tubular braid, a slit tube or any other suitable self-closing component. The capture element is sized to expand and cover the lumen of the vessel distal to the intended treatment area.

In one embodiment of the invention, a self-closing capture element is mounted adjacent the distal end of a standard-type steerable guidewire. The distal end of the capture element is fixed to the guidewire, while the proximal end can be pushed distally by a hollow deployment rod, thereby expanding the capture element. A latch is affixed to the guidewire to retain the capture element in the deployed configuration. The deployment rod can be removed and replaced with an interventional catheter, which is used to perform the desired treatment. To remove the capture device, a hollow, closing rod is exchanged for the interventional catheter. The closing rod disengages the latch so that the capture element can close around the guidewire and the assembly can be withdrawn. If the capture element is an occluder, then an aspiration catheter can be used to remove any trapped emboli before the capture element is closed and withdrawn. If the capture element is a filter, then any trapped emboli may simply be removed therewith.

In another embodiment of the invention, the capture element is a separate component that may be selectively loaded onto a corresponding guidewire. A deployment rod can advance the capture element along the guidewire to the distal treatment area, where further distal advancement the of the capture element distal end is blocked by a stop element on the guidewire. Further pushing by the deployment rod will advance the proximal end of the capture element towards the distal end until the device is deployed and a latch is engaged to retain the deployed configuration.

The device may optionally include a stop mechanism to prevent the ends of the capture element from being forced too close together, under which conditions, unwanted inversion of the structure could occur. Inversion of the capture element into a cup-shape can potentially prevent the self-closing feature that facilitates removal of the device.

Alternatively, in both of the embodiments discussed above, more than one latch may be mounted sequentially along the guidewire. Selective engagement of one of the latches will define the deployed length and the corresponding diameter of the capture element.

Braided filaments may be used in the invention to make either a filter or a support structure for a membrane. To provide a braided device of the invention with enhanced radiopacity, but with undiminished physical performance, radiopaque material is added to one or more braiding wires, in the centers thereof, where the effect on the physical properties of the wires is minimized.

BRIEF DESCRIPTION OF THE DRAWINGS

These and other features, aspects and advantages of the present invention will become better understood with reference to the following description, appended claims, and accompanying drawings where:

DETAILED DESCRIPTION OF THE INVENTION

Figure 1:
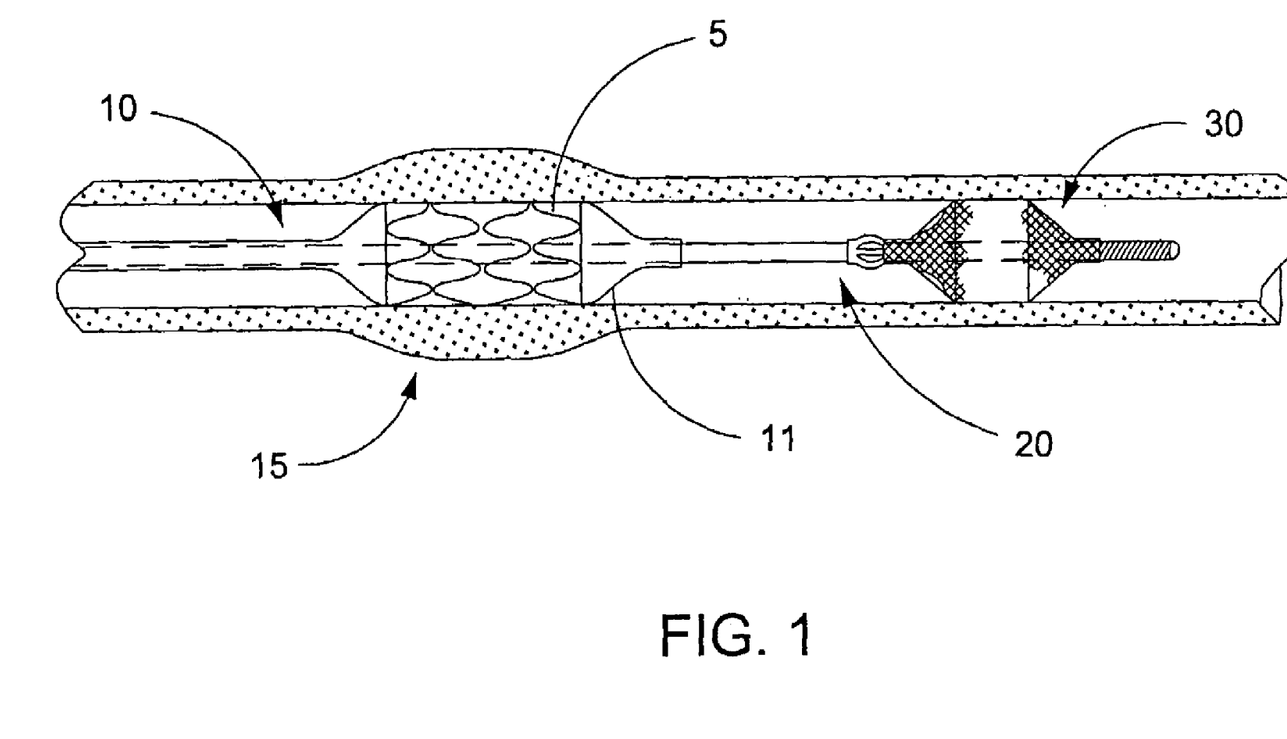
FIG. 1 is an illustration of a device in accordance with the invention, deployed within a blood vessel.
Figure 2:
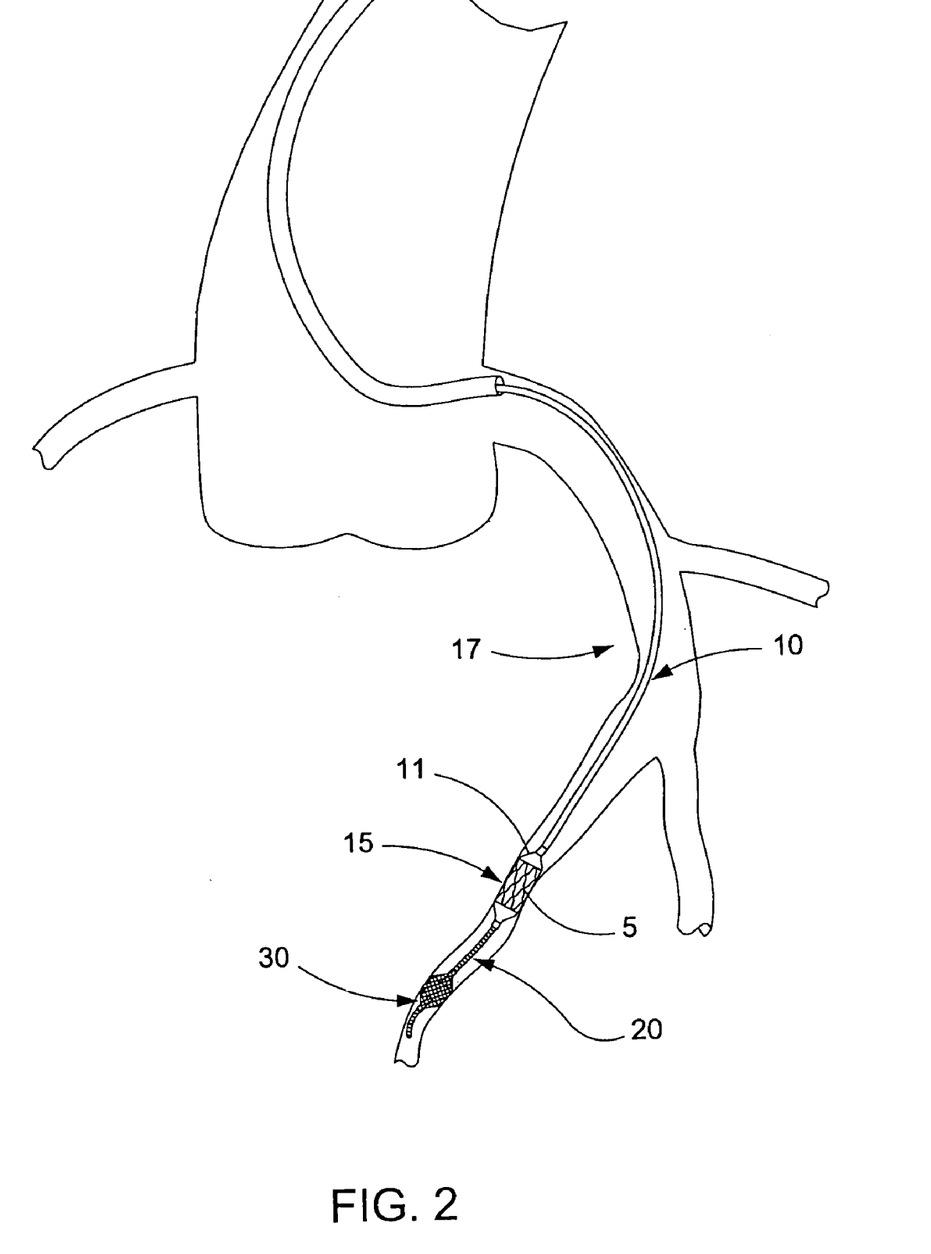
FIG. 2 is an illustration of a device in accordance with the invention, deployed within a portion of the coronary arterial anatomy.

The present invention is a temporary device for use during invasive procedures, such as interventional catheterizations or other procedures where the practitioner desires to capture embolic material that may be dislodged during the procedure. Intravascular procedures such as PTCA or stent deployment are often preferable to more invasive surgical techniques in the treatment of vascular narrowings, called stenoses or lesions. With reference to FIGS. 1 and 2, deployment of balloon expandable stent 5 is accomplished by threading catheter 10 through the vascular system of the patient until stent 5 is located within a stenosis at predetermined treatment site 15. Once positioned, balloon 11 of catheter 10 is inflated to expand stent 5 against the vascular wall to maintain the opening. Stent deployment can be performed following treatments such as angioplasty, or during initial balloon dilation of the treatment site, which is referred to as primary stenting. Catheter 10 is typically guided to treatment site 15 by a guidewire. In cases where the target stenosis is located in tortuous vessels that are remote from the vascular access point, such as coronary arteries 17 shown in FIG. 2, a steerable guidewire is commonly used.

Figure 3:
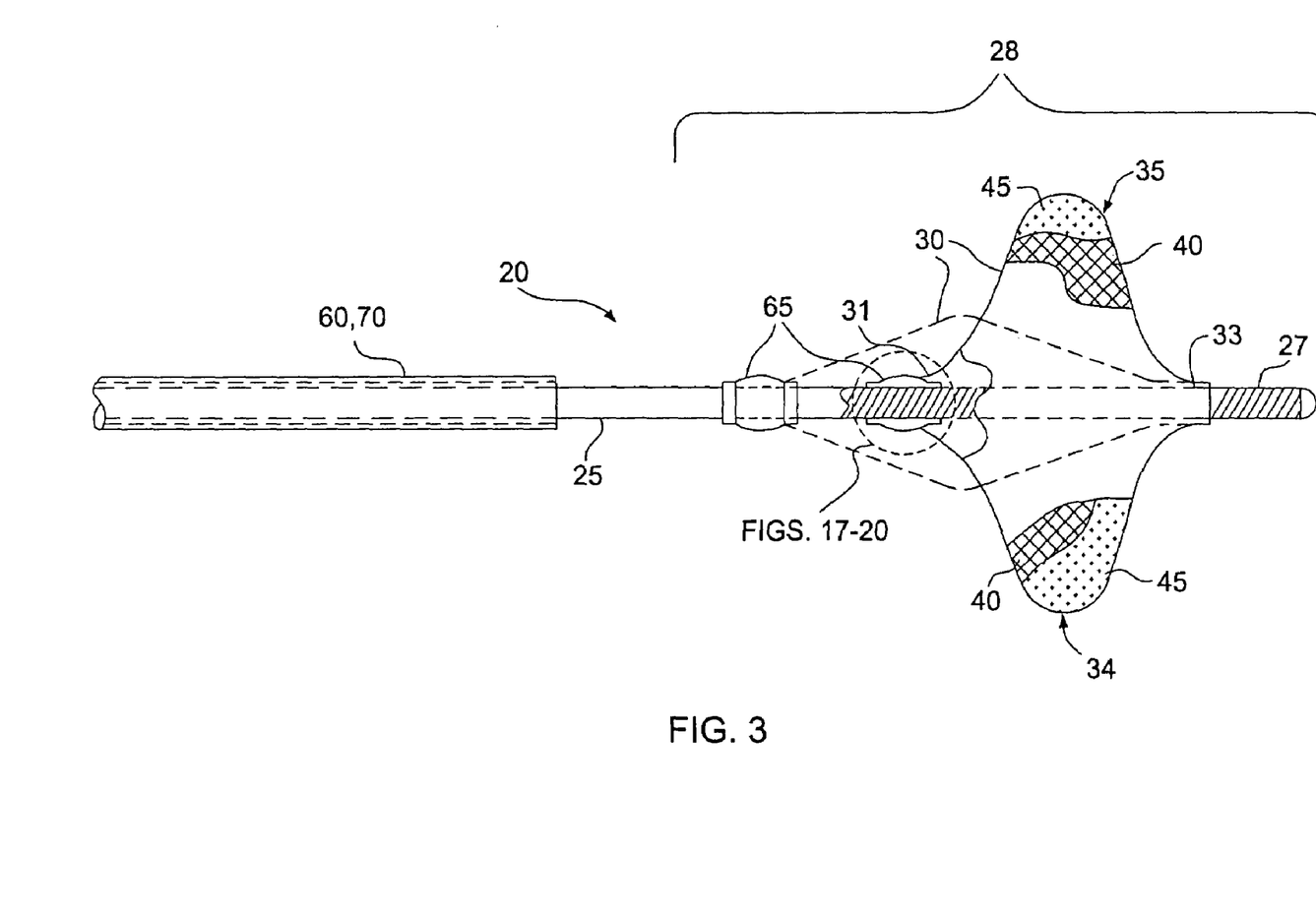
FIG. 3 is an illustration of a device in accordance with the invention, shown with a capture element in a deployed configuration and in an alternative deployed position.
Figure 4:
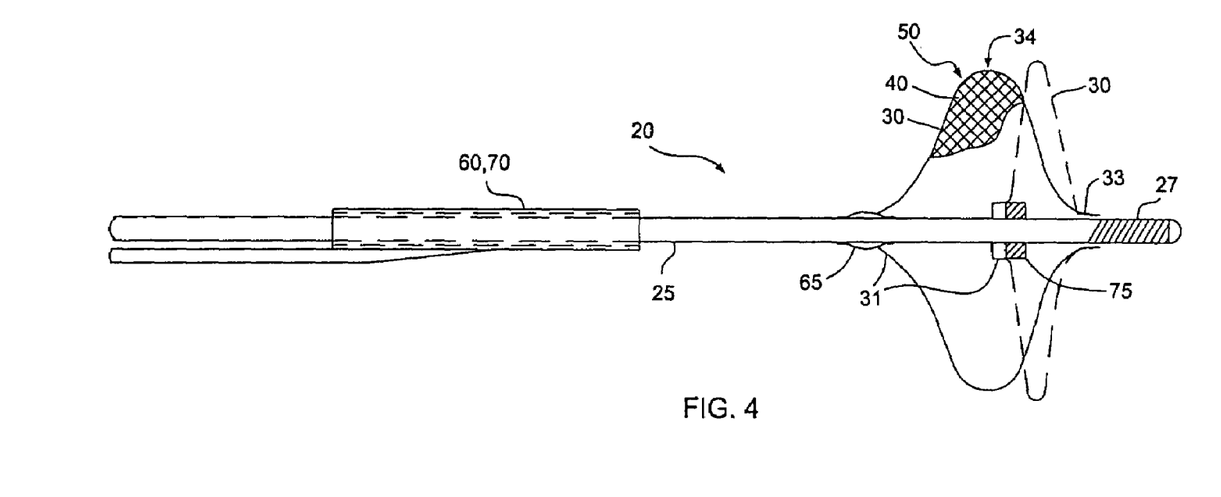
FIG. 4 is an illustration of a device in accordance with the invention, shown with a capture element in a deployed configuration and in an alternative position.
Figure 5:
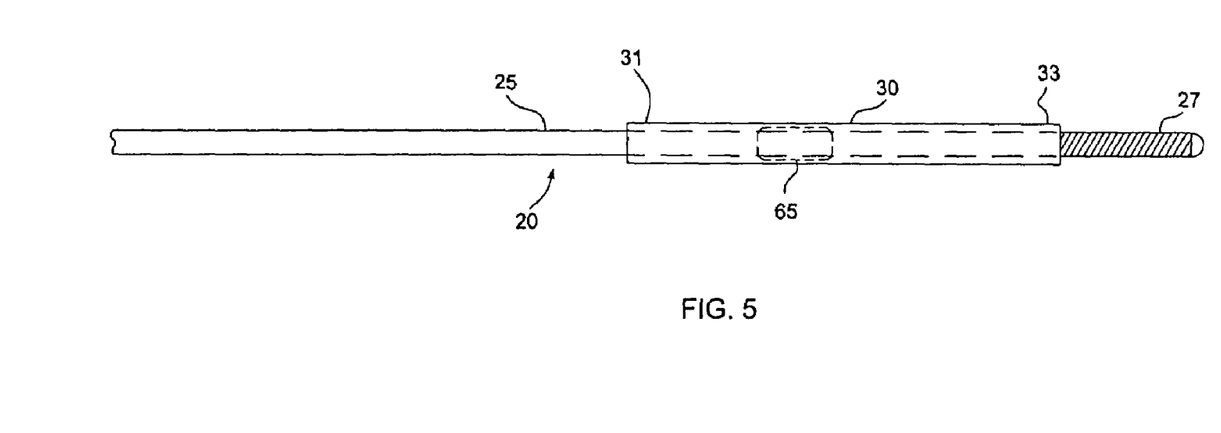
FIG. 5 is an illustration of a device in accordance with the invention, shown with a capture element in a closed configuration.

Referring to FIGS. 3–5, device 20 includes guidewire 25, having distal region 28 and distal end 27, which is preferably a coil spring that may extend the full length of distal region 28. Thin wires made from stainless steel and/or one of various alloys of platinum are commonly used to make such coil springs for use in guidewires. Guidewire 25 also comprises guidewire core 29. As shown in FIGS. 6–9, guidewire core 29 can be made from shape memory metal, such as nitinol, or is, preferably, a stainless steel wire tapered at the distal end. For treating small caliber vessels such as coronary arteries, core 29 will preferably measure about 0.006 inch (0.15 mm) in diameter. The length of distal region 28 may be selected as appropriate for the intended use of the filter guidewire. In one example, region 28 may be designed and intended to be flexible enough to negotiate tortuous coronary arteries, in which case the length of region 28 may be 15–35 cm (5.9–13.8 inches), preferably at least approximately 25 cm (9.8 inches). In comparison to treatment of coronary vessels, adaptations of the invention for treatment of renal arteries may require a relatively shorter region 28, and versions intended for approaching vessels in the head and neck may require a relatively longer region 28. When device 20 is designed for use in small vessels, guidewire 25 may have an outer diameter of about 0.014 inch (0.36 mm).

According to the present invention for capturing embolic material, a device generally designated as 20 guides catheter 10 to treatment site 15 and includes guidewire 25 and distally disposed capture element 30, which traps embolic debris that may be generated during the procedure. FIGS. 3–5 illustrate the invention as being directed to manipulating capture element 30, wherein relative movement of capture element proximal and distal ends 31, 33, respectively, either causes or accompanies transformation of capture element 30 between a closed configuration and an open, or deployed configuration. In the deployed configuration, capture element central region 34 expands into apposition with the targeted vessel. Transformation of capture element 30 may be impelled by external mechanical means, as will be discussed below, or by self-closing memory within capture element 30 itself. Such mechanical memory can be imparted to the metal comprising capture element 30 by thermal treatment to achieve a spring temper in stainless steel, for example, or to set a shape memory in a susceptible metal alloy such as a binary nickel-titanium (nitinol) alloy.

Figure 6:
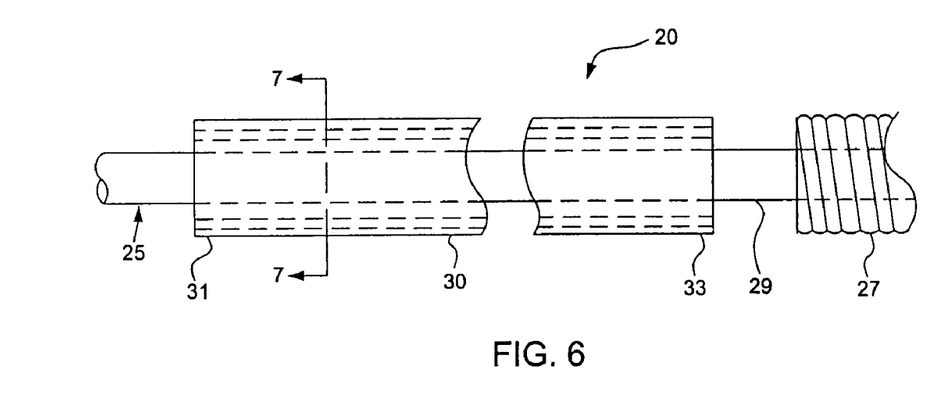
FIG. 6 is a longitudinal view of a portion of an embodiment in accordance with the invention, shown with a closed capture element being freely slidable over a guidewire.
Figure 7:
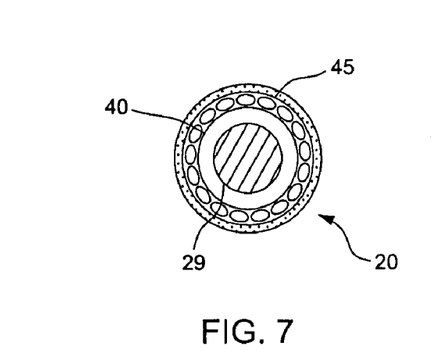
FIG. 7 is a transverse sectional view taken along the line 7—7 of FIG. 6.
Figure 8:
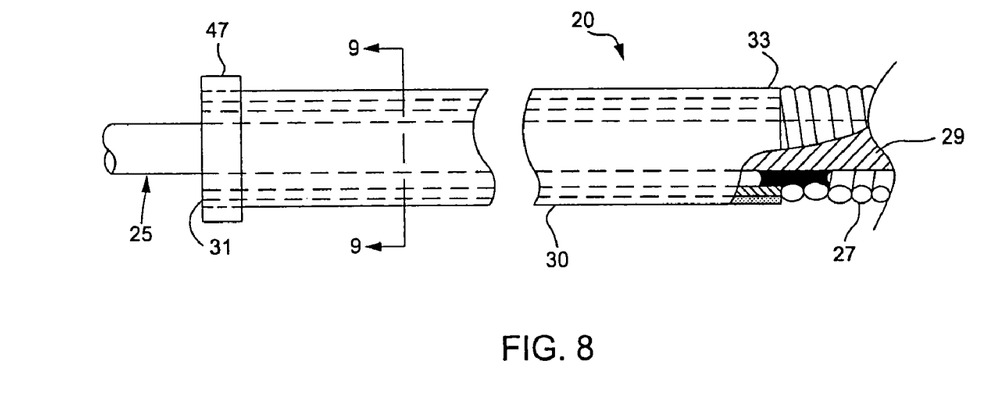
FIG. 8 is a longitudinal partial section of a portion of another embodiment in accordance with the invention, shown with a closed capture element being fixed to a guidewire.
Figure 9:
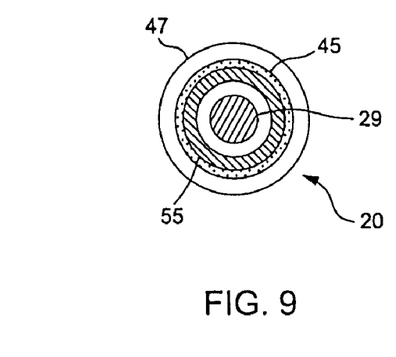
FIG. 9 is a transverse sectional view taken along the line 9—9 of FIG. 8.

In a first embodiment of the invention, as shown in FIG. 6, capture element 30 can be selectively loaded onto the proximal end of guidewire 25 and slidably advanced there along to a desired location within guidewire distal region 28. Capture element distal end 33 can be blocked from further distal advancement by a stop element such as guidewire distal end 27. In an alternative embodiment shown in FIG. 8, capture element 30 can be permanently pre-mounted to guidewire 25 by having capture element distal end 33 fastened to guidewire 25, preferably, with cyanoacrylate adhesive.

Transformation of self-closing capture element 30 from the closed configuration to the deployed configuration is induced by first advancing hollow deployment rod 60 over guidewire 25 until deployment rod 60 abuts capture element proximal end 31. While pulling on guidewire 25, rod 60 is then further advanced distally, pushing capture element proximal end 31 towards capture element distal end 33, thus expanding capture element central region 34 into apposition with the vessel. Capture element 30 is temporarily retained in the deployed configuration by the engagement of capture element proximal end 31 with latch 65. Once latch 65 is engaged, deployment rod 60 can be removed from guidewire 25 and exchanged for an interventional catheter, such as catheter 10. Upon completion of the treatment, catheter 10 can be exchanged for hollow closing rod 70. Closing rod 70 can be advanced over latch 65, disengaging it from capture element proximal end 31. Latch 65 will be described in further detail below. Withdrawal of closing rod 70 permits capture element 30 to close around guidewire 25.

Deployment rod 60 and closing rod 70 may have full length guidewire lumens or a rapid exchange type arrangement, as shown in FIG. 4. In the rapid exchange arrangement, deployment and closing rods 60, 70 have an elongate, wire-like, proximal shaft and a relatively short distal guidewire lumen. Various metals or polymers can be used to fabricate the hollow portions of the rods, although they are preferably made from thermoset polyimide tubing, available from sources such as HV Technologies, Inc., Trenton, Ga., U.S.A. Closing rod 70 may also be slidably disposed within deployment rod 60 to form a single catheter (not shown) for transformation of capture element 30, thus reducing the number of separate devices required to operate the invention. Such a catheter can provide the functions of either deployment rod 60 or closing rod 70, according to which of the rods is selectively extended distally of the other rod.

Capture element 30 is preferably occluder 35, as shown in FIG. 3, comprising a tube formed by braided filaments 40 and a covering of non-porous elastic membrane 45. Alternatively, capture element 30 may be filter 50, as shown in FIG. 4, wherein braided filaments 40 define pores and may have at least one inlet opening (not shown) that is substantially larger than the pores. Another alternative filter structure may comprise braided filaments 40, which provide support for a porous membrane (not shown), in which case the size of the filter pores is defined by the porous membrane rather than by braid filaments 40. Other types of assemblies that may be used in capture element 30 include an expandable strut structure 55. Strut structure 55 may be made from a first slotted or slit tube, covered with either a non-porous membrane 45 to provide an occluder, or a porous membrane (not shown) to provide a filter.

Optionally, adding radiopaque marker 47 to capture element proximal end 31 may aid in fluoroscopic observation of capture element 30 during manipulation thereof. Guidewire distal end 27 typically comprises a coil of radiopaque wire. Thus, the variable distance between radiopaque guidewire distal end 27 and radiopaque marker 47, as observed under fluoroscopy, can indicate whether capture element 30 is in the open or closed configuration. Alternatively, to enhance visualization of braided filaments 40 under fluoroscopy, at least one of the filaments may be a wire having enhanced radiopacity compared to conventional non-radiopaque wires suitable for braiding capture element 30. At least the majority of braided filaments 40 forming capture element 30 should be capable of being heat set into the desired tubular shape, and such wires should also have sufficient elastic properties to provide the desired self-closing features. Stainless steel and, preferably, nitinol monofilaments are suitable for braiding capture element 30. A braiding wire having enhanced radiopacity may be made of, or coated with, a radiopaque metal such as gold, platinum, tungsten, alloys thereof, or other biocompatible metals having a relatively high X-ray attenuation coefficient compared with stainless steel or nitinol. One or more filaments having enhanced radiopacity may be inter-woven with non-radiopaque wires, or all wires comprising capture element 30 may have the same enhanced radiopacity.

Figure 10:
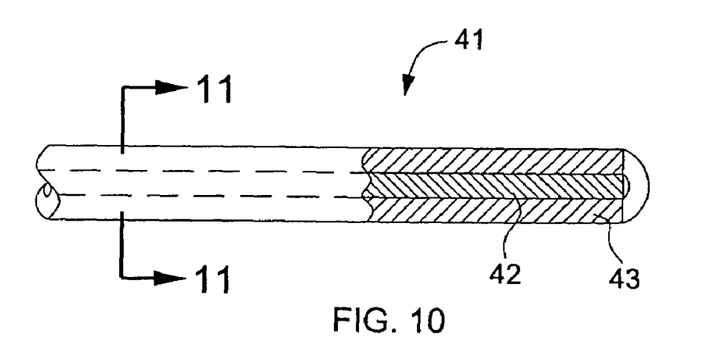
FIG. 10 is a longitudinal partial section of a portion of enhanced radiopacity wire used in making a filter in accordance with the invention.
Figure 11:
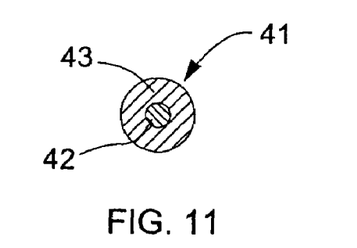
FIG. 11 is a transverse sectional view taken along the line 11—11 of FIG. 10.
Figure 12:
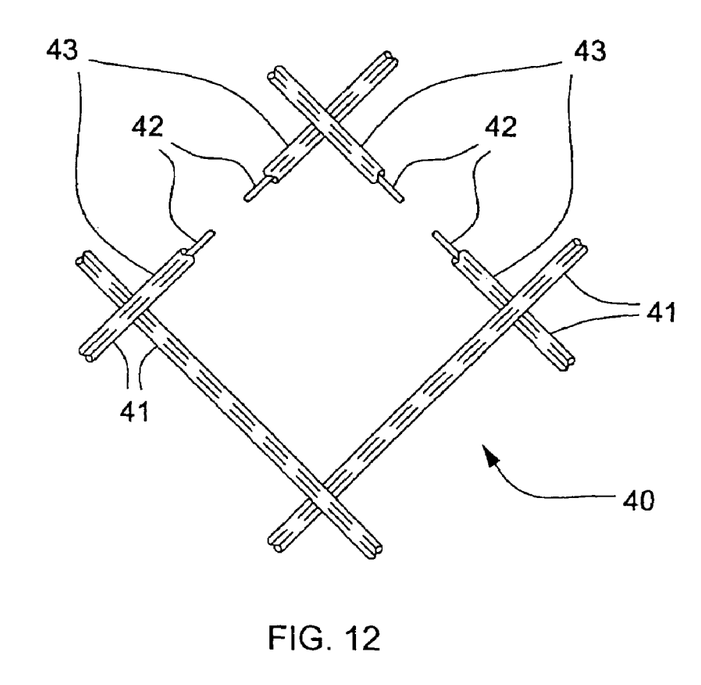
FIG. 12 is a portion of a braided device in accordance with the invention, with portions of enhanced radiopacity braiding wire exposed.

FIGS. 10–12 illustrate another embodiment for enhancing visualization of the invention under x-rays, in which one or more braided filaments 40 may comprise composite wire 41 having radiopaque core 42 and non-radiopaque layer or casing 43. Such coaxial, composite wires are referred to as DFT (drawn-filled-tube) wires in the metallic arts, and are formed by inserting a solid billet of one metal into a hollow billet of a different metal, then repeatedly drawing and annealing the combination until a wire of desired diameter and hardness is achieved. A preferred DFT wire for use in the instant invention comprises a core of a 90% platinum-10% nickel alloy, and a casing of binary nickel-titanium (nitinol) alloy. By placing the more radiopaque, but more ductile material in the center of wire 41, the nitinol outer layer is able to provide the resulting wire with nearly undiminished mechanical properties, as compared with nitinol monofilament wire. Conversely, placing a radiopaque coating or layer around a nitinol core substantially effects the physical properties of the wire. Thus, in comparison to nitinol monofilament wire, PtNi core/nitinol tube DFT wire has a greater X-ray attenuation coefficient and nearly identical mechanical properties. Wire 41, comprising a PtNi core/nitinol tube combination, provides improved radiopacity of capture element 30 without giving up the shape-memory or pseudo-elastic properties of nitinol, which contribute to good shape-retention and the elastic transformation of capture element 30 between opened and closed configurations. In the preferred DFT combination of wire 41, core 42 makes up at least approximately 25% of the total cross-section of wire 41, by area. In making capture element 30 in a size intended for use in vessels up to about 6 mm in diameter, braided filaments 40 are preferably about 0.001–0.003 inch (0.03–0.08 mm) diameter, more preferably about 0.002 inch (0.05 mm) diameter. Such wires are available from Fort Wayne Metals Corp., Fort Wayne, Ind., U.S.A.

Figure 13:
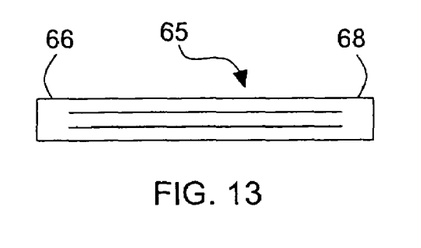
FIG. 13 is an illustration of a latch in accordance with the invention, shown in a closed configuration.
Figure 14:
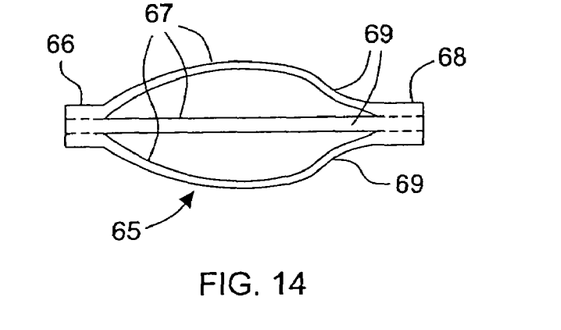
FIG. 14 is an illustration of a latch in accordance with the invention, shown in an open configuration.

Latch 65 is recoverable, or self-expanding into a normal shape and size that is engageable with capture element proximal end 31. In the preferred embodiment, shown in FIGS. 13–14, latch 65 comprises a second tube that has been slotted or slit, then heat-set in an expanded form to create two or more generally longitudinal pawl elements 67. FIG. 13 depicts latch 65 in a closed or compressed form, and FIG. 14 depicts latch 65 in an open form. Latch 65 is preferably made from slit nitinol tubing, but in an alternative embodiment, latch 65 can comprise a self-expanding section of braided tubing, which does not require slits or pawls. Latch 65 can be considered to be mechanically similar to capture element 30 in that relative movement of latch proximal end 66 and latch distal end 68 either causes or accompanies transformation of latch 65 between a closed configuration and an open, or normal, configuration. Latch proximal end 66 is bonded to guidewire 25, while latch distal end 68 is unattached thereto, thus permitting relative movement between latch proximal and distal ends 66, 68, as may be required during transformation of latch 65 between a closed configuration and an open configuration.

Figure 15:
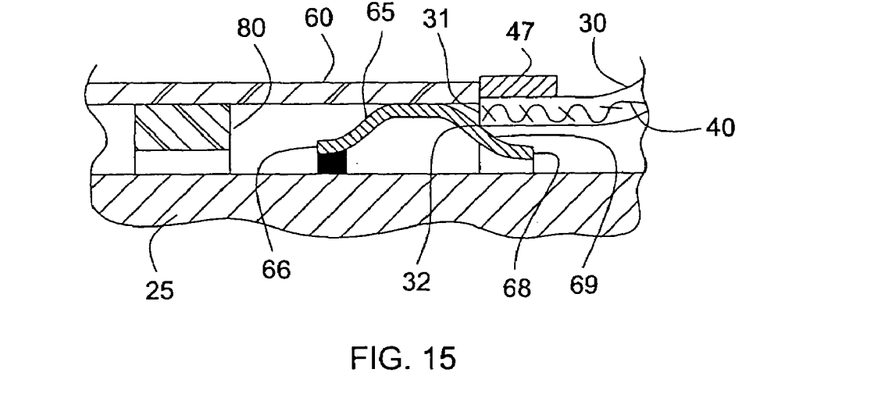
FIG. 15 is a longitudinal section of a portion a device in accordance with the invention, shown during deployment with a hollow deployment rod.

FIG. 15 shows deployment rod 60 having pushed capture element proximal end 31 sufficiently distally such that latch 65 has expanded radially outward and inner edge 32 of capture element proximal end 31 has engaged with latch engagement surface 69, located on the distal portion of latch 65. The inside diameter of deployment rod 60 is larger than the diameter of inner edge 32, such that edge 32 is exposed to latch engagement surface 69 while rod 60 pushes capture element 30 into the deployed configuration. Latch 65 provides secure retention of capture element 30 in its deployed configuration until latch 65 is disengaged from capture element 30 by closing rod 70. To provide such security, latch engagement surface 69 is angled or tapered with respect to guidewire 25 such that any increase in proximally directed force between capture element proximal end 31 and latch 65 will only serve to increase the engagement there between. For example, such an increase in force may further transform latch 65 into a more open configuration, thus increasing the angle between latch engagement surface 69 and guidewire 25.

Figure 16:
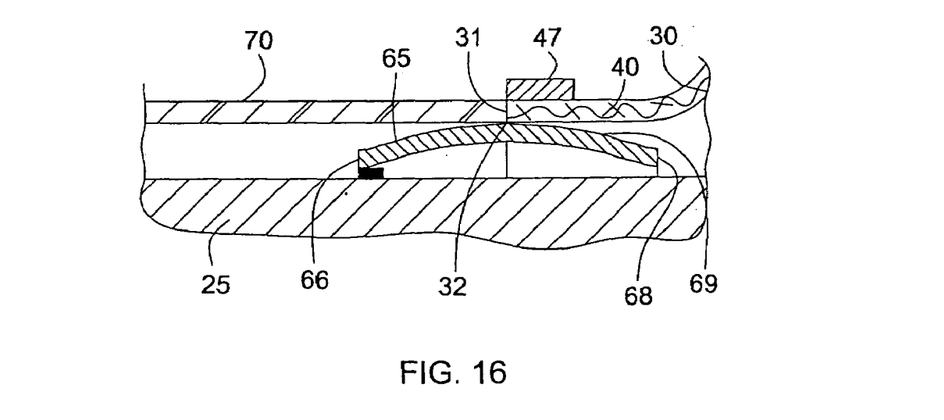
FIG. 16 is a longitudinal section of a portion of a device in accordance with the invention, shown during closing with a hollow closing rod.

FIG. 16 shows closing rod 70 having been advanced over latch 65, at least partially closing latch 65 and thus disengaging capture element proximal end 31 there from. In the embodiment shown, the inside diameter of closing rod 70 is generally no larger than the diameter of inner edge 32, thus preventing latch 65 from opening sufficiently to attain engagement there between. Upon closing of latch 65, capture element 30 will begin to close itself, moving capture element proximal end 31 proximally until it abuts the distal end of closing rod 70. Thereafter, further closing of capture element 30 is controlled by the withdrawal of closing rod 70. Alternatively, the components of the invention may be constructed such that closing rod 70 fits slidingly in an annular space between latch 65 and capture element proximal end 31. In this alternative embodiment (not shown), when rod 70 releases latch 65, self-closing of capture element 30 causes capture element proximal end 31 to slide proximally over rod 70, without being controlled thereby.

According to the invention, device 20 may optionally incorporate two or more latches 65 disposed along guidewire 25, as shown in FIG. 3. In capture element 30, the overall length corresponds inversely to the deployed diameter. Thus, a single capture element 30 may be selectively deployed and retained at different sizes by advancing capture element proximal end 31 into engagement with different latches 65 disposed at spaced-apart locations within distal region 28. For example, to achieve the deployed configuration shown in FIG. 3, deployment rod 60 can push capture element proximal end 31 over the relatively proximal latch 65, at which moment capture element 30 would take the form shown in alternative position (in broken lines). As determined by the operative clinician, deployment rod 60 can be withdrawn to leave capture element proximal end 31 engaged with the relatively proximal latch 65, or rod 60 can be further advanced there over until capture element proximal end 31 is pushed over and engaged with the relatively distal latch 65, thus transforming capture element 30 into the deployed configuration shown.

Figure 17:
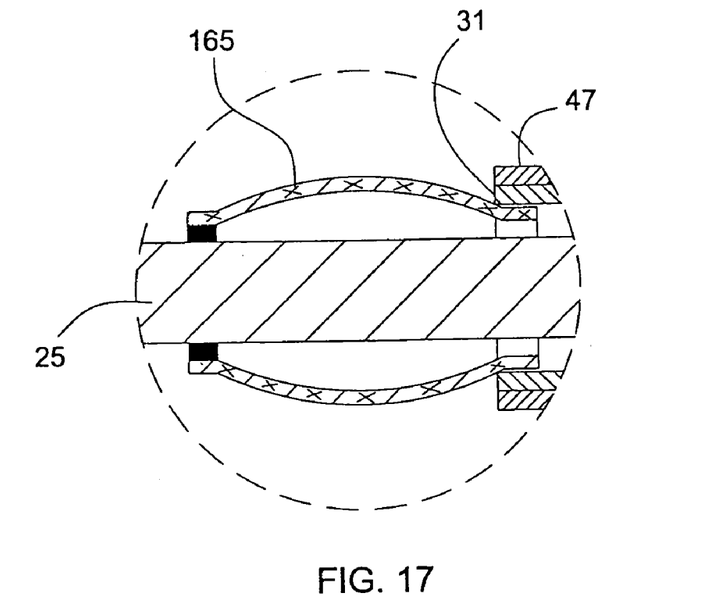
FIGS. 17–20 are enlarged, longitudinal sections of portions of devices in accordance with the invention, showing several alternative embodiments of latches.
Figure 18:
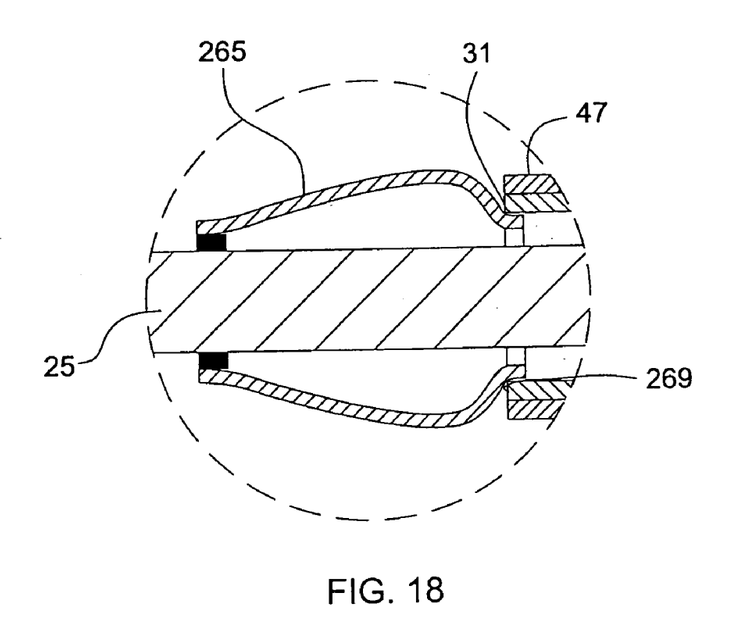
Figure 19:
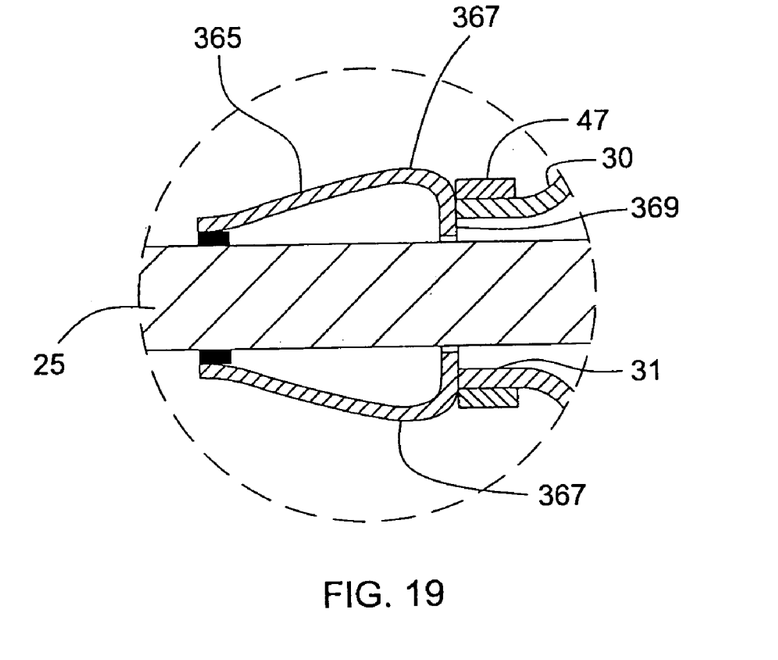
Figure 20:
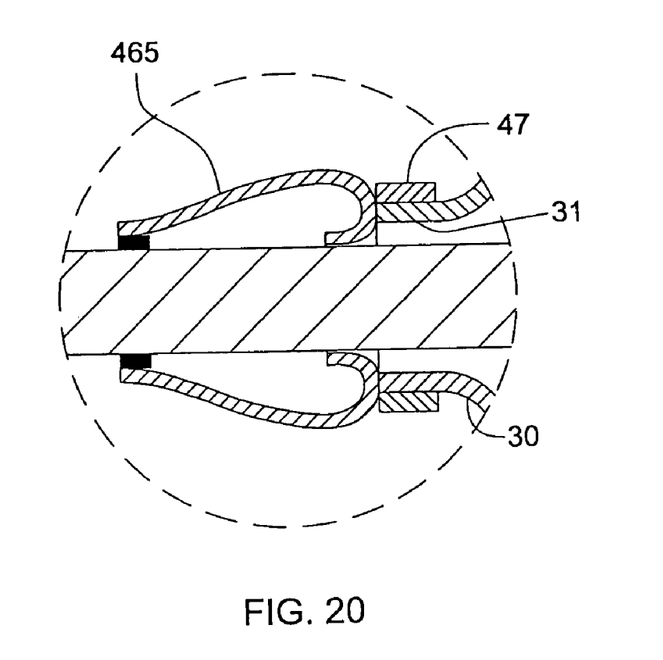

FIGS. 17–20 are enlarged illustrations of embodiments that are alternatives to latch 65 in accordance with the invention. FIG. 17 depicts latch 165, which comprises a self-expanding tubular braid. FIG. 18 depicts latch 265, which is made from slit tubing, and wherein latch engagement surface 269 forms an angle approaching perpendicular to the axis of guidewire 25. FIG. 19 depicts latch 365 wherein latch engagement surface 369 is perpendicular to the axis of guidewire 25 and wherein pawl elements 367 are not circumferentially joined at their distal ends. FIG. 20 depicts latch 465 in an open configuration, and in which latch 465 is similar to latch 365, except that the pawl distal ends are inverted. To close latch 465 requires folding the latch more tightly upon itself, rather than having the distal and proximal ends move farther apart.

FIG. 4 illustrates the function of anti-inversion stops in the invention. Capture element 30 is shown in an alternate position (in broken lines), wherein first anti-inversion stop 75 limits the distal advancement of capture element proximal end 31, which may be pushed by either deployment or closing rods 60, 70. If capture element ends 31, 33 are pushed too close together, then capture element 30 can invert into a cup shape, which may prevent self-closure of capture element 30 and the expeditious withdrawal of device 20. First stop 75 is preferably a polyimide tube or ring that is fixed about guidewire 25 at a location between capture element ends 31, 33.

FIG. 15 shows second anti-inversion stop 80, which is fixed within deployment rod 60 adjacent the distal end thereof. Second stop 80 may be included within either deployment or closing rods 60, 70. The inner diameter of stop 80 is sized to slide over guidewire 25, but not to slide over latch 65 or its alternative embodiments, thus limiting the distal travel of rods 60, 70. Restricting movement of rods 60, 70 in this manner prevents further advancement of capture element proximal end 31, and avoids inversion of capture element 30. Second stop 80 may be a separate ring of material, as shown, or it may be a necked portion (not shown) of the tubing that forms deployment or closing rods 60, 70. Alternatively, deployment or closing rods 60, 70 may have a stepped change in wall thickness (not shown) to create second stop 80 at the appropriate location within rods 60, 70.

If multiple latches 65 are incorporated into device 20, then it is preferred to use first anti-inversion stop 75 rather than second anti-inversion stop 80. In this case, first stop 75 would be mounted between capture element distal end 33 and most distally located latch 65. This is because, for example, second stop 80 could prevent deployment rod 60 from advancing over more proximally located latch(es) 65, as required to selectively deploy capture element 30 in relatively larger configurations.

The methods of using of the inventive temporary device for capturing embolic material will be described below. In a first example, device 20, having self-closing capture element 30 pre-mounted adjacent the distal end thereof, is advanced into the patient's vasculature until capture element 30 is beyond the intended treatment site. Deployment rod 60 is advanced over guidewire 25 until rod 60 abuts capture element proximal end 31, which is then pushed over and into engagement with latch 65. With capture element 30 deployed into apposition with the vessel wall, deployment rod 60 is withdrawn. Next, therapeutic catheter 10 is advanced over guidewire 25 to the intended treatment site, and therapy, such as balloon angioplasty, is performed. Any embolic debris generated during the therapy is trapped by capture element 30. After the therapy is completed, therapeutic catheter 10 is prepared for withdrawal, as by deflating the balloon, if so equipped, and catheter 10 is withdrawn. Closing rod 70 is advanced over guidewire 25 until latch 65 is closed. Last, withdrawal of closing rod 70 allows capture element 30 to close, and all devices are removed from the patient. Although the steps above describe the use of deployment rod 60 and closing rod 70 to introduce and withdraw device 20, it should be understood that variations are possible, since any tubular device, including therapeutic catheter 10 can operate latch 65, either during introduction or withdrawal. Optionally, using interventional catheter 10 to close latch 65 after therapy is complete can simplify the method by eliminating the need for closing rod 70. Similarly, catheter 10 could be used instead of deployment rod 60 to deploy capture element 30 immediately before beginning therapy. It will be understood that catheter 10 can also be of the rapid exchange type to facilitate interchanging rods 60, 70 and catheter 10.

In a second example of methods of using the invention, guidewire 25, without having capture element 30 mounted thereon, is advanced into the patient's vasculature until distal region 28 is beyond the intended treatment site. If so elected by the operative clinician, capture element 30 is placed over the proximal end of guidewire 25. Deployment rod 60 subsequently is placed over guidewire 25 and is used to push capture element 30 along guidewire 25 to distal region 28. When capture element distal end 33 encounters a stop element on guidewire 25, further pushing by rod 60 against capture element proximal end 31 deploys capture element 30 and engages capture element proximal end 31 with latch 65. Subsequent steps of the method are comparable to those described in the first example above.

The first and second examples above describe methods that are suitable when capture element 30 traps and holds embolic material, as is possible with filter 50, because the embolic material will be removed within filter 50. Alternatively, when capture element 30 simply blocks the passage of embolic material, but does not collect it, as is done with occluder 35, then an additional aspiration step is required before closing and removing occluder 35. In this case, therapeutic catheter 10 is exchanged for an aspiration catheter (not shown), and any contaminated fluid is removed from the area adjacent occluder 35 before capture element 30 is closed and device 20 is withdrawn. Optionally, catheter 10 may have a built-in aspiration lumen, such that aspiration can be performed without requiring a catheter exchange.

While the invention has been particularly shown and described with reference to the preferred embodiments thereof, it will be understood by those skilled in the art that various changes in form and detail may be made there in without departing from the spirit and scope of the invention. For example, the invention may be used in any intravascular treatment utilizing a guidewire where the possibility of loosening emboli may occur. Although the description herein illustrates angioplasty and stent placement procedures as significant applications, it should be understood that the present invention is in no way limited to those environments.

We claim:

1. A temporary device for capturing embolic material from a bodily fluid within a vessel of a patient, the device comprising:
   an elongate guidewire having a distal region;
   a capture element disposed about the guidewire distal region, the capture element having distal and proximal ends and a central region, wherein relative longitudinal movement between the distal and proximal ends accompanies a transformation of the capture element between a generally tubular closed configuration and a deployed configuration wherein the central region is expanded into apposition with the vessel; and
   at least one latch fixed to the guidewire distal region and being releasably engageable with the proximal end of the capture element to temporarily retain the capture element in the deployed configuration.

2. The device of claim 1 wherein the distal end of the capture element is longitudinally fixed to the guidewire.

3. The device of claim 1 wherein the capture element is removably slidable along the guidewire, the capture element having been selectively placed about the guidewire and pushed onto the guidewire distal region, the device further comprising a stop element disposed on the guidewire distal region, the stop element being capable of blocking advancement distal thereto by the distal end of the capture element.

4. The device of claim 1 wherein the at least one latch is positioned between the distal and proximal ends of the capture element when the capture element is in the closed configuration.

5. The device of claim 1 further comprising a first anti-inversion stop fixed to the guidewire at a location distal of the at least one latch, the first anti-inversion stop being capable of preventing advancement distal thereto by the proximal end of the capture element.

6. The device of claim 1 further comprising an elongate, hollow, deployment rod slidably and removably disposed about the guidewire, the deployment rod being operable to push the proximal end of the capture element distally along the guidewire and over the at least one latch, thereby effectuating the transformation of the capture element from the closed configuration to the deployed configuration.

7. The device of claim 6 wherein the deployment rod comprises an elongate, wire-like, proximal shaft and a relatively short tubular distal section.

8. The device of claim 6 wherein the deployment rod comprises an interventional catheter.

9. The device of claim 1 wherein the capture element comprises a filter operable, when in the deployed configuration, to allow the bodily fluid to pass there through while simultaneously capturing the embolic material therefrom.

10. The device of claim 9 wherein the capture element comprises a tubular braid of filaments.

11. The device of claim 10 wherein the filaments comprise shape-memory metal wire.

12. The device of claim 11 wherein the shape-memory metal is nitinol.

13. The device of claim 1 wherein the capture element comprises a support structure capable of the transformation between the closed and deployed configurations, the support structure being covered with an elastic membrane.

14. The device of claim 13 wherein the support structure comprises a tubular braid of filaments.

15. The device of claim 13 wherein the support structure comprises a first tube having been slotted or slit to form generally longitudinal struts.

16. The device of claim 15 wherein the first tube comprises nitinol.

17. The device of claim 13 wherein the elastic membrane is porous, such that the capture element comprises a filter operable, when in the deployed configuration, to allow the bodily fluid to pass therethrough while simultaneously capturing the embolic material therefrom.

18. The device of claim 13 wherein the elastic membrane comprises natural rubber, synthetic rubber, thermoplastic elastomer or thermoset polymer.

19. The device of claim 1 wherein the at least one latch has distal and proximal ends, and a normal shape and size suitable for engagement with the proximal end of the capture element, the at least one latch being reversibly operable to allow the proximal end of the capture element to slide there over.

20. The device of claim 19 wherein the proximal end of the at least one latch is fixed to the guidewire.

21. The device of claim 19 wherein the at least one latch comprises a tubular braid of filaments.

22. The device of claim 19 wherein the normal shape of the at least one latch comprises one or more latch engagement surfaces for engagement with the proximal end of the capture element.

23. The device of claim 22 wherein the one or more latch engagement surfaces are circumferentially arranged in a middle region of the at least one latch.

24. The device of claim 19 further comprising an elongate, hollow, closing rod slidably and removably disposed about the guidewire, the closing rod being operable to advance over at least a portion of the at least one latch to selectively compress the normal shape and size thereof, thereby disengaging the latch from the proximal end of the capture element.

25. The device of claim 24 wherein the closing rod comprises an elongate, wire-like, proximal shaft and a relatively short tubular distal section.

26. The device of claim 24 wherein the closing rod comprises an interventional catheter.

* * * * *